(12) United States Patent
Tsuchimoto

(10) Patent No.: US 11,406,268 B2
(45) Date of Patent: Aug. 9, 2022

(54) BODY TEMPERATURE MEASURING DEVICE

(71) Applicant: Murata Manufacturing Co., Ltd., Nagaokakyo (JP)

(72) Inventor: Hirofumi Tsuchimoto, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 377 days.

(21) Appl. No.: 16/663,857

(22) Filed: Oct. 25, 2019

(65) Prior Publication Data

US 2020/0060553 A1 Feb. 27, 2020

Related U.S. Application Data

(63) Continuation of application No. PCT/JP2018/016535, filed on Apr. 24, 2018.

(30) Foreign Application Priority Data

Apr. 27, 2017 (JP) .............................. JP2017-088565

(51) Int. Cl.
 *A61B 5/01* (2006.01)
 *A61B 5/00* (2006.01)
 (Continued)

(52) U.S. Cl.
 CPC .............. *A61B 5/01* (2013.01); *A61B 5/7221* (2013.01); *A61B 5/7264* (2013.01); *A61B 5/746* (2013.01);
 (Continued)

(58) Field of Classification Search
 None
 See application file for complete search history.

(56) References Cited

U.S. PATENT DOCUMENTS 4,465,077 A * 8/1984 Schneider .......... A61B 10/0012
 600/551
9,015,001 B2 * 4/2015 Shimizu ................ G01K 1/165
 702/131
(Continued)

FOREIGN PATENT DOCUMENTS

JP 2000088659 A 3/2000
JP 2003235813 A 8/2003
(Continued)

OTHER PUBLICATIONS

International Search Report issued in PCT/JP2018/016535, dated Jul. 31, 2018.

(Continued)

*Primary Examiner* — Benjamin S Melhus
(74) *Attorney, Agent, or Firm* — ArentFox Schiff LLP

(57) ABSTRACT

A body temperature measuring device includes a temperature detector including a first thermal resistor and a first pair of temperature sensors that sandwich the thermal resistor and continuously detect temperature data, and a second thermal resistor and a second pair of temperature sensors that sandwich the second thermal resistor and continuously detect temperature data. Moreover, an equilibrium state determination component determines whether the temperature detector is thermally in an equilibrium state based on detected temperature data, and a body temperature acquisition component acquires body temperature data based on temperature data detected when the temperature detector is in a thermal equilibrium state and a physical property value of the thermal resistors.

19 Claims, 14 Drawing Sheets

(51) Int. Cl.
*G01K 7/16* (2006.01)
*G01K 13/00* (2021.01)
*G01K 13/20* (2021.01)

(52) U.S. Cl.
CPC ............... *G01K 7/16* (2013.01); *G01K 13/20* (2021.01); *A61B 2562/0271* (2013.01)

(56) References Cited

U.S. PATENT DOCUMENTS

| | | | | |
|---|---|---|---|---|
| 9,528,887 | B2* | 12/2016 | Shimizu | G01K 7/42 |
| 10,750,951 | B1* | 8/2020 | Prachar | A61B 5/6804 |
| 2005/0245839 | A1* | 11/2005 | Stivoric | A61B 5/0008 |
| | | | | 600/549 |
| 2006/0056487 | A1* | 3/2006 | Kuroda | G01K 13/20 |
| | | | | 374/179 |
| 2007/0295713 | A1* | 12/2007 | Carlton-Foss | A61B 5/01 |
| | | | | 219/497 |
| 2011/0317737 | A1* | 12/2011 | Klewer | G01K 1/16 |
| | | | | 374/29 |
| 2014/0149065 | A1* | 5/2014 | Pompei | A61B 5/7282 |
| | | | | 702/131 |
| 2017/0049397 | A1* | 2/2017 | Sun | A61B 5/01 |
| 2017/0071581 | A1* | 3/2017 | Sacks | G01K 1/02 |
| 2018/0008149 | A1* | 1/2018 | Pekander | A61B 5/0008 |
| 2018/0242850 | A1* | 8/2018 | Ellis | G16H 40/67 |
| 2019/0142280 | A1* | 5/2019 | Bongers | A61B 5/742 |
| | | | | 600/549 |

FOREIGN PATENT DOCUMENTS

| | | |
|---|---|---|
| JP | 2004163391 A | 6/2004 |
| JP | 2008128781 A | 6/2008 |
| JP | 2014038489 A | 2/2014 |

OTHER PUBLICATIONS

Written Opinion of the International Searching Authority issued in PCT/JP2018/016535, dated Jul. 31, 2018.

* cited by examiner

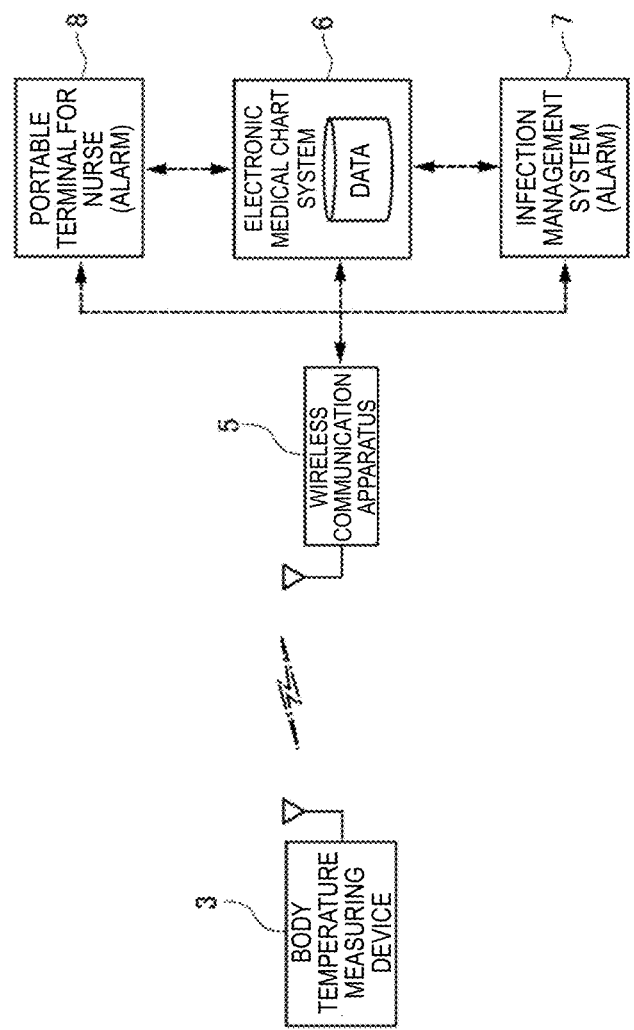

BODY TEMPERATURE MEASURING DEVICE

CROSS REFERENCE TO RELATED APPLICATIONS

The present application is a continuation of PCT/JP2018/016535 filed Apr. 24, 2018, which claims priority to Japanese Patent Application No. 2017-088565, filed Apr. 27, 2017, the entire contents of each of which are incorporated herein by reference.

TECHNICAL FIELD

The present invention relates to a body temperature measuring device and, more particularly, to a body temperature measuring device for continuously a measuring body temperature (deep body temperature).

BACKGROUND

Currently, there are proposed techniques for measuring body temperature (i.e., deep body temperature) by continuously detecting a body surface temperature. For example, Patent Document 1 (identified below) discloses a wearable temperature measuring device for estimating a body temperature, such as an oral temperature, based on time-series body surface temperature data (for example, body surface temperature data of a subject measured during sleeping).

More specifically, the wearable temperature measuring device includes a body surface temperature detecting unit for detecting the temperature of the body surface, an auxiliary body surface temperature detecting unit for accessorially detecting the temperature of the body surface affected by the outside air, and an outside air temperature detecting unit for detecting the outside air temperature, and an inverse calculation model that is constructed by a PLS regression analysis using a body surface temperature data group and body temperature measured in advance. The wearable temperature measuring device estimates the body temperature from a temperature data group in which temperature detection data detected by each temperature detecting unit is arranged in time-series by using the inverse calculation model.

According to this wearable temperature measuring device, since the body temperature is estimated from the body surface temperature data group by using the inverse calculation model, the wearable temperature measuring device can be easily used even when the health care of the subject is performed based on the daily body temperature, for example. Further, since the body temperature is estimated from the body surface temperature detection data measured for several hours using the inverse calculation model, the influence of the fluctuation in the measurement can be suppressed compared to the case where the body temperature such as the oral temperature is directly measured.

Patent Document 1: Japanese Unexamined Patent Application Publication No. 2008-128781.

Incidentally, a body surface temperature varies greatly due to disturbance such as the outside air temperature. That is, for example, when a sudden temperature change occurs, such as when moving from a warm room to a cold outside, the body surface temperature will also vary greatly.

Accordingly, in the above-described wearable temperature measuring device of Patent Document 1, although the body temperature is estimated by using the inverse calculation model constructed by the PLS regression analysis, there is a risk that the influence of disturbance cannot be appropriately eliminated since the function of accurately correcting (i.e., compensating) the influence of the disturbance such as the outside air temperature in principle is not provided. In addition, in the above-described wearable temperature measuring device, since the body temperature is estimated from the body surface temperature detection data measured for several hours using the inverse calculation model, there is a risk that it is difficult to grasp heat generation or the like in a relatively short time (span), or the grasping is delayed.

SUMMARY OF THE INVENTION

The exemplary embodiments of the present invention have been made to solve the above problems, and an object of the present invention is to provide a body temperature measuring device configured to appropriately eliminate an influence of disturbance and configured to grasp heat generation in a shorter time (span).

Thus, a body temperature measuring device according to an exemplary aspect includes a temperature detection section with thermal resistor and a plurality of temperature sensors that sandwich the thermal resistor and continuously detects temperature data, an equilibrium state determination unit that determines whether or not the temperature detection section is thermally in an equilibrium state based on detected temperature data, and a body temperature acquisition unit that acquires body temperature data based on temperature data detected when the temperature detection section is determined to be in a thermal equilibrium state by the equilibrium state determination unit and a physical property value of the thermal resistor.

According to the body temperature measuring device of the exemplary aspect, it is determined whether or not the temperature detection section (e.g., a plurality of temperature sensors) is thermally in an equilibrium state (e.g., a state where there is no variation in thermal flow rate), and body temperature data is acquired based on temperature data detected when the temperature detection section is determined to be in a thermal equilibrium state and a thermal resistance value of the thermal resistor. For this reason, for example, even though the temperature detection section temporarily is made into a non-equilibrium state due to such as a sudden change (e.g., disturbance) in the ambient temperature with a person entering or exiting a room or the like, it is possible to recognize the non-equilibrium state being reached (e.g., in the non-equilibrium state), thereby removing inaccurate temperature data (noise). Further, since noise (e.g., temperature data in the non-equilibrium state) can be removed as described above, it is not necessary to smooth data by providing a low pass filter or the like having a large time constant, for example. As a result, the influence of disturbance can be appropriately eliminated, and heat generation can be grasped in a shorter time (span).

According to the exemplary aspects of the present invention, the influence of disturbance can be eliminated and heat generation can be grasped in a shorter time period (span).

BRIEF DESCRIPTION OF DRAWINGS

FIG. 14 is a block diagram illustrating an overall configuration of an intra-hospital system to which the body temperature measuring device according to the third exemplary embodiment is applied.

DESCRIPTION OF EMBODIMENTS

Figure 1:
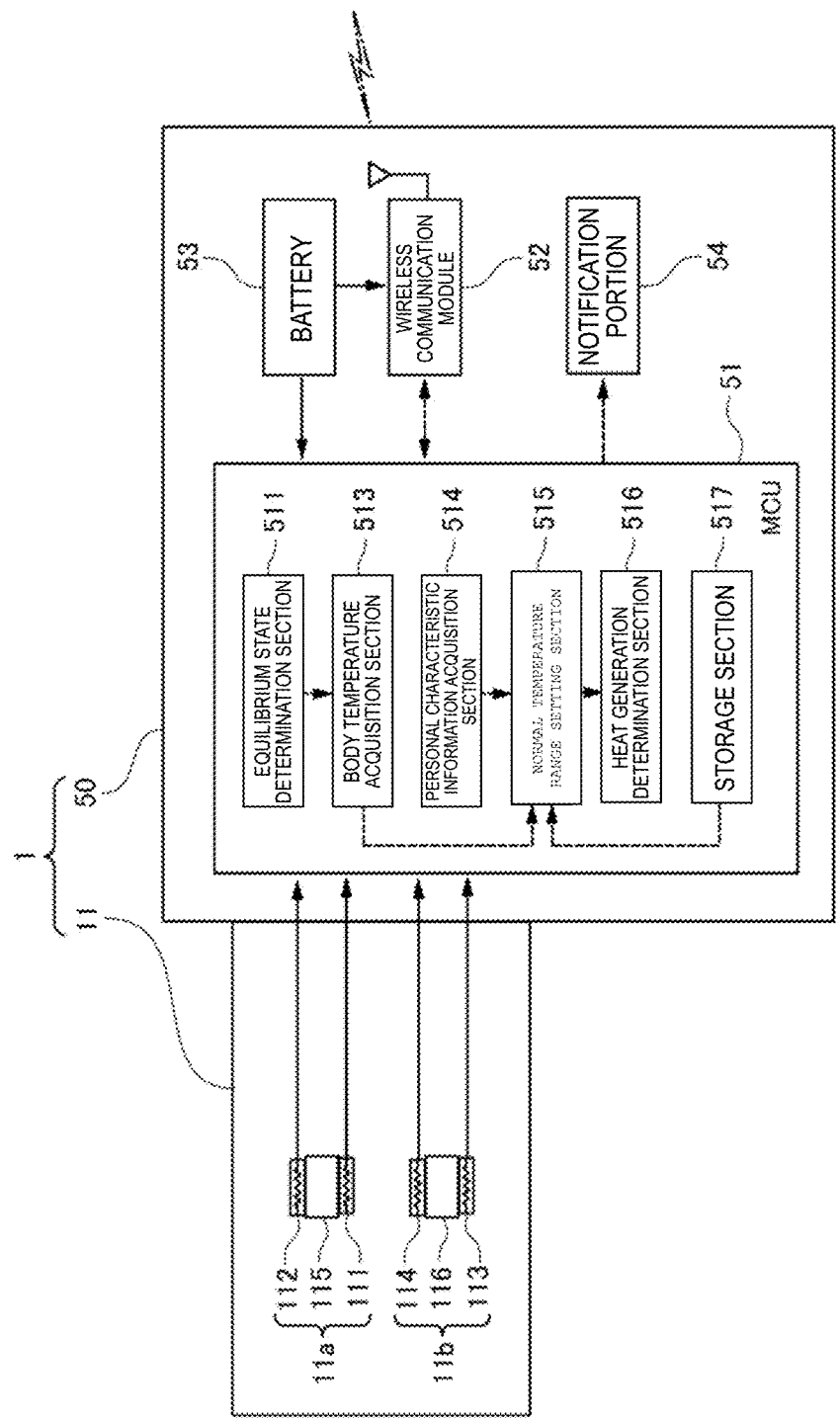
FIG. 1 is a block diagram illustrating a functional configuration of a body temperature measuring device according to a first exemplary embodiment.

Hereinafter, exemplary embodiments of the present invention will be described in detail with reference to the accompanying drawings. In the drawings, the same reference signs are used to designate the same or corresponding parts. In the drawings, the same elements are denoted by the same reference signs, and the description thereof will not be repeated.

First Exemplary Embodiment

Figure 2:
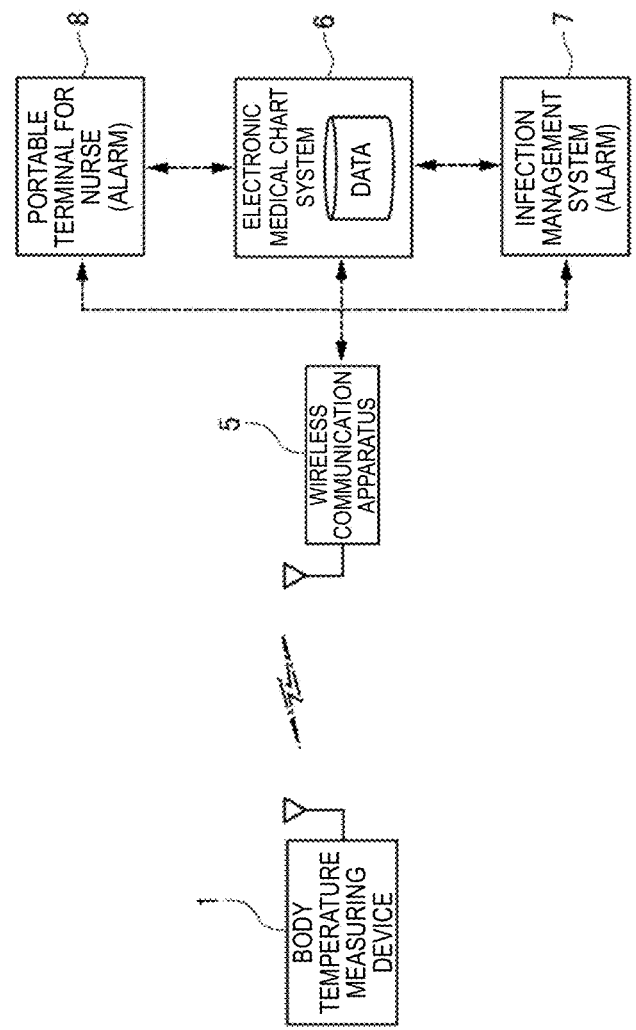
FIG. 2 is a block diagram illustrating an overall configuration of an intra-hospital system to which the body temperature measuring device according to the first exemplary embodiment is applied.
Figure 3:
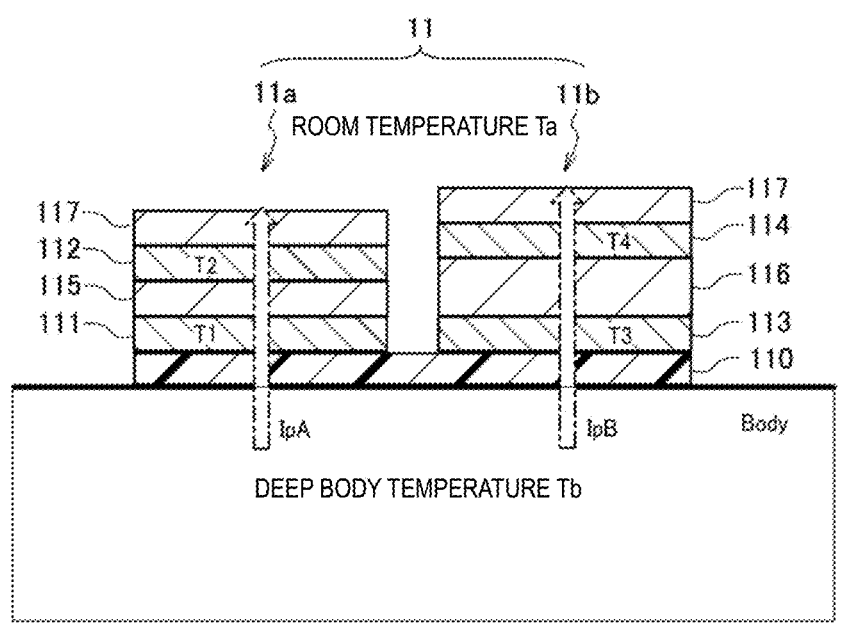
FIG. 3 is a diagram illustrating a configuration of a temperature detection section constituting the body temperature measuring device according to the first exemplary embodiment.

A configuration of a body temperature measuring device 1 according to a first exemplary embodiment will be described with reference to FIG. 1 to FIG. 3 together. Here, a case where the body temperature measuring device 1 is applied to, for example, an intra-hospital system (e.g., electronic medical chart system 6 and infection management system 7) will be described as an example. FIG. 1 is a block diagram illustrating a functional configuration of the body temperature measuring device 1. FIG. 2 is a block diagram illustrating an overall configuration of an intra-hospital system to which the body temperature measuring device 1 is applied. FIG. 3 is a diagram illustrating a configuration of a temperature detection section 11 constituting the body temperature measuring device 1.

In an exemplary aspect, the body temperature measuring device 1 includes the temperature detection section (simply referred to as a "temperature detector", which can be a non-heating type deep body thermometer, for example) 11 that can be coupled to a body surface and configured to detect a temperature, and a temperature information processing unit 50 (e.g., a processor) that is configured to acquire a deep body temperature based on a temperature detected by the temperature detection section 11. Here, the temperature detection section 11 includes a flexible substrate 110 and two sets of sensing portions 11a and 11b. Further, in the exemplary aspect, the temperature information processing unit 50 includes an MCU 51, a wireless communication module 52, a battery 53, and a notification portion 54. Hereinafter, the constituent elements will be described in detail.

The temperature detection section 11 is configured to be stuck or coupled to a body surface of a user to detect a temperature of the body surface or the like of the user. As described above, the temperature detection section 11 includes the two sets of sensing portions 11a and 11b (also simply referred to as "sensors"). One sensing portion 11a is configured to include a thermal resistor 115 (e.g., a "first thermal resistor") having a predetermined thermal resistance value and a pair of temperature sensors (e.g., a "first pair of temperature sensors"), that is, a first temperature sensor 111 and a second temperature sensor 112 mounted in or on, for example, the flexible substrate (film substrate) 110 having flexibility and arranged so as to sandwich the thermal resistor 115 in a thickness direction thereof. It is noted that each of the first temperature sensor 111 and the second temperature sensor 112 may be embedded in, for example, the thermal resistor 115.

The other sensing portion 11b is configured to include a thermal resistor 116 (e.g., a "second thermal resistor") having a thermal resistance value different from that of the thermal resistor 115, and a pair of temperature sensors (e.g., a "second pair of temperature sensors"), that is, a third temperature sensor 113 and a fourth temperature sensor 114 mounted in or on the flexible substrate (film substrate) 110 and arranged so as to sandwich the thermal resistor 116 in a thickness direction thereof. It is noted that the third temperature sensor 113 and the fourth temperature sensor 114 each may be embedded in, for example, the thermal resistor 116. Also, each of the two sets of sensing portions 11a and 11b further include a sheet-like heat-insulating member 117 disposed so as to cover the second temperature sensor 112, and a sheet-like heat-insulating member 117 disposed so as to cover the fourth temperature sensor 114.

The thermal resistors 115 and 116 are formed in a rectangular thin sheet shape having a predetermined thickness, for example. It is noted that the shape of each of the thermal resistors 115 and 116 is not limited to a rectangular shape, and may be a circular shape or the like, for example. The thermal resistors 115 and 116 are formed of a material having thermal insulation properties, for example, a polyethylene foam, a urethane foam, or the like. Further, the thermal resistors 115 and 116 have flexibility along the shape and movement of the body surface. In consideration of thermal insulation properties and flexibility, it is preferable that a thickness of the thermal resistors 115 and 116 be, for example, about from 0.1 mm to several mm. In particular, the thermal resistance value of the thermal resistor 115 is set to be different from the thermal resistance value of the thermal resistor 116. It should be appreciated that the thermal resistance value of each of the thermal resistors 115 and 116 can be adjusted by, for example, changing the thickness or the like of the thermal resistor.

Since two sets of sensing portions 11a and 11b using the thermal resistors 115 and 116 having different thermal resistance values are included, namely, two systems of heat flow systems having different thermal resistance values are formed, a term of a thermal resistance RB of the human body can be canceled so that the body temperature (deep body temperature) can be obtained even though the thermal resistance RB of the human body is unknown. Therefore, since the deep body temperature can be acquired without assuming the thermal resistance RB of the human body, even though the thermal resistance RB of each user is different, the deep body temperature can be acquired with higher accuracy. It is noted that a method for canceling the thermal resistance RB of the human body will be described later.

According to exemplary aspects, the temperature sensors 111 to 114 can be, for example, a thermistor, a temperature measuring resistor, or the like, whose resistance value varies depending on temperature. Preferably, the temperature sensors 111 to 114 have a thermal capacitance as small as possible from the viewpoint of enhancing responsiveness. Therefore, for example, a chip thermistor is preferably used as the temperature sensors 111 to 114. Each of the four temperature sensors 111 to 114 is electrically connected to the temperature information processing unit 50 (i.e., MCU 51) via a printed wiring, and electric signals (e.g., voltage values) corresponding to the temperature are read by the temperature information processing unit 50 (MCU 51).

The temperature information processing unit 50 is configured to include the micro control unit (MCU) 51, the wireless communication module 52, the battery 53, the notification portion 54, and the like.

As described above, the four temperature sensors 111 to 114 are connected to the temperature information processing unit 50 (MCU 51), and the detection signal (temperature data) output from each of the temperature sensors 111 to 114 is input to the temperature information processing unit 50 (MCU 51).

The temperature information processing unit 50 is configured to obtain body temperature (deep body temperature) based on a thermal resistance value of the thermal resistor 115 forming one sensing portion 11a, a detected temperature of the first temperature sensor 111, a detected temperature of the second temperature sensor 112, a thermal resistance value of the thermal resistor 116 forming the other sensing portion 11b, a detected temperature of the third temperature sensor 113, and a detected temperature of the fourth temperature sensor 114. It is noted that the details will be described later. In addition, in order to obtain body temperature (deep body temperature), instead of thermal resistance values of the thermal resistor 115 and the thermal resistor 116, for example, physical property values such as thermal capacitance, specific heat, density, shape and the like of the thermal resistor 115 and the thermal resistor 116 may be used.

In particular, the temperature information processing unit 50 is configured to appropriately eliminate the influence of disturbance, and has a function of grasping heat generation in a shorter time (span). Therefore, the temperature information processing unit 50 functionally includes an equilibrium state determination section 511, a body temperature acquisition section 513, a personal characteristic information acquisition section 514, a normal temperature range setting section 515, a heat generation determination section 516, and a storage section (memory) 517. According to an exemplary aspect, in the temperature information processing unit 50, a program stored in the ROM or the like is executed by the MCU 51, whereby the functions of the equilibrium state determination section 511, the body temperature acquisition section 513, the personal characteristic information acquisition section 514, the normal temperature range setting section 515, and the heat generation determination section 516 can be provided to perform the algorithms described herein.

The equilibrium state determination section 511 is configured to determine whether or not the temperature detection section 11 (i.e., the temperature sensors 111 to 114) is thermally in an equilibrium state (e.g., a state where there is no variation in thermal flow rate) by using an equilibrium state determination equation. More specifically, the equilibrium state determination section 511 determines whether or not the temperature detection section 11 is thermally in the equilibrium state by using the following equilibrium state determination equation (1). Namely, when assuming that the temperature data detected by the first temperature sensor 111 is T1, the temperature data detected by the second temperature sensor 112 is T2, the temperature data detected by the third temperature sensor 113 is T3, and the temperature data detected by the fourth temperature sensor 114 is T4, the equilibrium state determination section 511 determines that the temperature detection section 11 (temperature sensors 111 to 114) is thermally in the equilibrium state when the equilibrium state determination equation (1) is satisfied. On the other hand, when the equilibrium state determination equation (1) is not satisfied, the equilibrium state determination section 511 determines that the temperature detection section 11 (the temperature sensors 111 to 114) is not thermally in the equilibrium state (in a non-equilibrium state).

$$T3-T4>T1-T2, T3>T1 \tag{1}$$

It is noted that when a temperature Ta in a hospital can be acquired from the electronic medical chart system 6 (or the infection management system 7), for example, the temperature detection section 11 (four temperature sensors 111 to 114) may be determined whether or not to be thermally in the equilibrium state, in further consideration of the following equilibrium state determination equations (2), (3), and (4). In this case, in addition to the above equilibrium state determination equation (1), when all of the equilibrium state determination equations (2), (3) and (4) are satisfied, it is determined that the temperature detection section 11 (the temperature sensors 111 to 114) is thermally in the equilibrium state. On the other hand, when any one of the equilibrium state determination equations (1) to (4) or all of the equilibrium state determination equations (1) to (4) are not satisfied, it is determined that the temperature detection section 11 (temperature sensors 111 to 114) is not thermally in the equilibrium state (in the non-equilibrium state).

$$dTa>dT4 \tag{2}$$

$$K(T1-T2)-(T3-T4)>0 \text{ (when } Ta>Tb) \tag{3}$$

$$K(T1-T2)-(T3-T4)\leq 0 \text{ (when } Ta\leq Tb) \tag{4}$$

It is noted that a constant K is the ratio of thermal resistance in two thermal flows.

Further, instead of (or in addition to) the above equilibrium state determination equations (1) to (4), it is also possible to determine whether or not the temperature detection section 11 (temperature sensors 111 to 114) is thermally in the equilibrium state by using the following equilibrium state determination equations (5) to (8). In this case, when at least one equilibrium state determination equation of the following equilibrium state determination equations (5) to (8) is satisfied, it is determined that the temperature detection section 11 (temperature sensors 111 to 114) is thermally in the equilibrium state. On the other hand, when all the following equilibrium state determination equations (5) to (8) are not satisfied, it is determined that the temperature detection section 11 (temperature sensors 111 to 114) is not thermally in the equilibrium state (in the non-equilibrium state).

$$\Delta T3 < a \qquad (5)$$

(Where a is a predetermined value, such as 0.2 (° C./min).)

$$\Delta T1 < a \qquad (6)$$

(Where a is a predetermined value, such as 0.2 (° C./min).)

$$\Delta T3 < \Delta T4 \qquad (7)$$

$$\Delta T1 < \Delta T2 \qquad (8)$$

The determination result (i.e., information about whether or not the temperature detection section 11 is thermally in the equilibrium state) by the equilibrium state determination section 511 is output to the body temperature acquisition section 513.

The body temperature acquisition section 513 obtains body temperature data (e.g., deep body temperature) based on a thermal resistance value RpA of the thermal resistor 115 stored in advance, the detected temperature T1 of the first temperature sensor 111, the detected temperature T2 of the second temperature sensor 112, a thermal resistance value RpB of the thermal resistor 116 stored in advance, the detected temperature T3 of the third temperature sensor 113, and the detected temperature T4 of the fourth temperature sensor 114. In particular, the body temperature acquisition section 513 is configured to acquire body temperature data based on temperature data detected when the temperature detection section 11 is determined to be in a thermal equilibrium state.

More specifically, the body temperature acquisition section 513 is configured to first perform temperature compensation calculation on the detected temperature data to calculate a body temperature data candidate (or a correction value). Next, based on the determination result of the thermal equilibrium state, the body temperature acquisition section 513 is configured to remove the body temperature data candidate (or the correction value) obtained from the temperature data detected when being in the non-equilibrium state, and acquire regular body temperature data. The following will be explained in more detail.

Using the following equations (9) and (10), the body temperature acquisition section 513 is configured to erase the unknown thermal resistance RB by comparing the thermal flows of two systems having different thermal resistors (thermal resistance), and calculate (or estimate) the body temperature data candidate Tb of a user (human body) having the unknown thermal resistance RB.

$$IpA=(T1-T2)/RpA=(Tb-T1)/RB \qquad (9)$$

$$IpB=(T3-T4)/RpB=(Tb-T3)/RB \qquad (10)$$

It is noted that RpA and RpB are thermal resistances (known) of the thermal resistors 115 and 116.

When the thermal resistance RB of the user (human body) is known, the body temperature data candidate can be calculated (or estimated) by one of the sensing portions 11a (or 11b). More specifically, when assuming that the body temperature data candidate of the human body is Tb, the detected temperature of the first temperature sensor 111 is T1, the detected temperature of the second temperature sensor 112 is T2, and the equivalent thermal resistance from the deep portion of the human body to the body surface is RB, and the equivalent thermal resistance in the thickness direction of the thermal resistor 115 is RpA, the body temperature data candidate Tb in the state where the thermal equilibrium state is reached can be expressed by the following equation (11).

$$Tb=T2+\{RpA/(RB+RpA)\}(T1-T2) \qquad (11)$$

Therefore, when the thermal resistance RB of the human body is known, or by setting, for example, a general (normal) thermal resistance value as the thermal resistance RB of the human body, the deep body temperature Tb can be obtained from the temperature T1 detected by the first temperature sensor 111 and the temperature T2 detected by the second temperature sensor 112.

Figure 5:
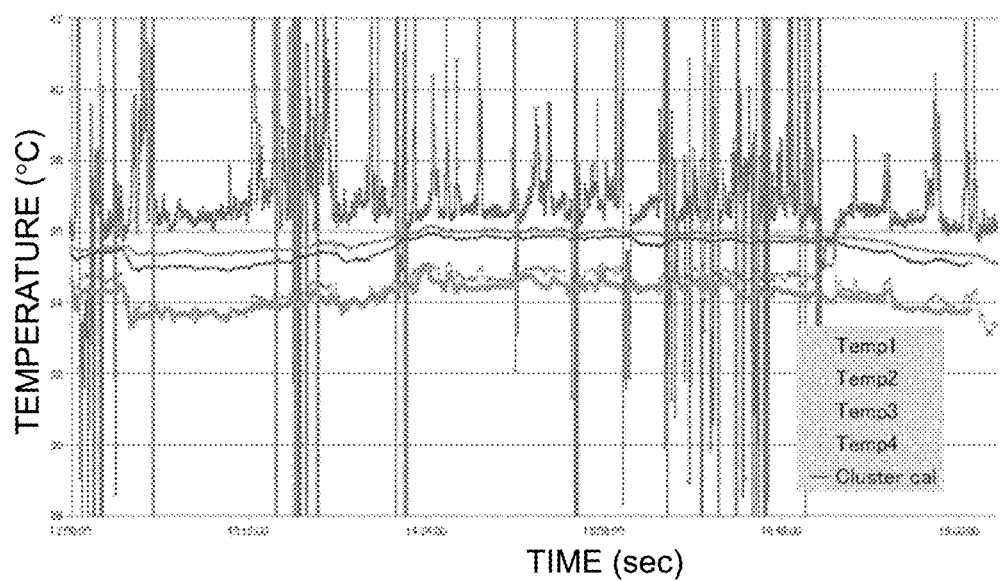
FIG. 5 is a diagram illustrating an example of a body temperature data candidate (thermal flow compensation calculation result) before an equilibrium state determination is performed.
Figure 6:
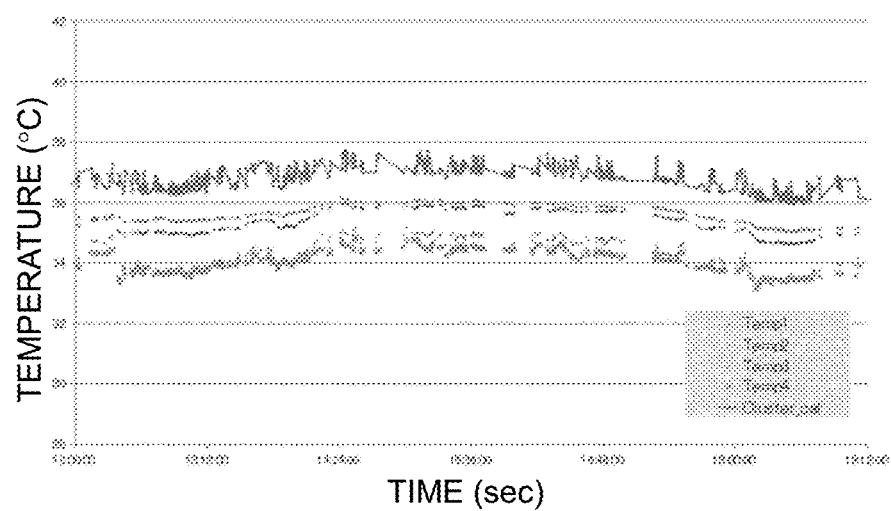
FIG. 6 is a diagram illustrating an example of body temperature data (thermal flow compensation calculation result) after the equilibrium state determination is performed.

Next, based on the thermal equilibrium state determination result described above, the body temperature acquisition section 513 is configured to remove the body temperature data candidate obtained from the temperature data detected when it is thermally in the non-equilibrium state, and to acquire the body temperature data candidate obtained from the temperature data detected when it is thermally in the equilibrium state as regular body temperature data. Here, FIG. 5 illustrates an example of a body temperature data candidate (e.g., a thermal flow compensation calculation result) before the equilibrium state determination is performed (i.e., before the body temperature data candidate obtained from the temperature data detected in the non-equilibrium state is removed). Further, FIG. 6 illustrates an example of body temperature data (e.g., thermal flow compensation calculation result) after the equilibrium state determination is performed (i.e., after the body temperature data candidate obtained from the temperature data detected in the non-equilibrium state is removed). In FIGS. 5 and 6, the horizontal axis represents time, and the vertical axis represents temperature (in ° C.). As illustrated in FIG. 5 and FIG. 6, the body temperature data candidate (noise) obtained from the temperature data (inaccurate temperature data) detected when the temperature detection section 11 is in the non-equilibrium state are removed.

According to the exemplary aspect, the body temperature data (deep body temperature Tb) acquired by the body temperature acquisition section 513 is output to the heat generation determination section 516, the wireless communication module 52, and the storage section 517.

The personal characteristic information acquisition section 514 is configured to acquire the personal characteristic information (for example, age, sex, height, weight, and the like) of the user. The personal characteristic information of the user can be acquired from the electronic medical chart system 6 or the like via, for example, wireless communication (e.g., wireless communication apparatus 5 and wireless communication module 52). Further, an input I/F such as a touch panel may be provided, and a configuration may be such that information is input from the input I/F. The personal characteristic information of the user acquired by the personal characteristic information acquisition section 514 is stored in the storage section 517, and is output to the normal temperature range setting section 515 as necessary.

The normal temperature range setting section 515 sets a normal temperature range (e.g., an expected value range of a normal temperature) of the user. More specifically, the normal temperature range setting section 515 sets the normal temperature range (the expected value range of the normal temperature) of the user in association with the time of the day (at each time). Further, the normal temperature range setting section 515 is configured to set the normal temperature range (the expected value range of the normal temperature) of the user based on the user's personal characteristic information from statistical data belonging to the same category as that of the user. More specifically, the normal temperature range setting section 515 sets, for example, "Ave±3σ" as the normal temperature range (the expected value range of the normal temperature) from statistical data (for example, average Ave and standard deviation σ) of a person belonging to the same category (for example, the same age or sex) as the user.

Here, the statistical data (average and standard deviation) described above is acquired from the electronic medical chart system 6 or the like in advance via, for example, wireless communication (wireless communication apparatus 5 and wireless communication module 52), and is stored in the storage section 517. For example, a configuration can be provided in which the function of the normal temperature range setting section 515 is provided on the electronic medical chart system 6 side, and the normal temperature range (the expected value range of the normal temperature) of the user is set on the electronic medical chart system 6 side.

Furthermore, it is preferable that the normal temperature range setting section 515 learn the body temperature data of the user acquired in the past and stored in the storage section 517, and set (or correct) the normal temperature range of the user in consideration of a learned learning value. In general, the normal temperature varies 1° C. or more in a day, and also varies depending on the personal characteristics such as age and sex, and moreover differs in individuals. In contrast, according to the embodiment, the normal temperature range (the expected value range of the normal temperature) is set in consideration of the variation in the day and the personal characteristics such as the age and sex, and the personal difference is corrected by using the learned value (learning result). The normal temperature range (the expected value range of the normal temperature) of the user set by the normal temperature range setting section 515 is output to the heat generation determination section 516.

The heat generation determination section 516 is configured to determine (detects) whether or not the body temperature is within the normal temperature range (whether or not the body temperature is abnormal). The determination result (information about whether or not the user's body temperature is within the normal temperature range) by the heat generation determination section 516 is output to the notification portion 54.

The notification portion 54 can include, for example, an LCD display or a buzzer (or a speaker), and is configured to notify the user and/or an administrator (such as a doctor or a nurse in the embodiment) that the body temperature data is out of the normal temperature range when the body temperature data falls outside the normal temperature range. When the body temperature deviates from the normal temperature range (Ave±3σ), the notification portion 54 outputs, for example, warning display or warning sound (alarm or beep sound). It is noted that it is preferable that the notification portion 54 transmit notification information (warning information) to the electronic medical chart system 6 via the wireless communication (wireless communication module 52 and wireless communication apparatus 5). When the notification information (warning information) is received, the electronic medical chart system 6 issues an output request for warning display or warning sound (alarm or beep sound) to a portable terminal 8 (for a nurse) and the infection management system 7 (for a doctor) which are electrically connected. Thus, the body temperature abnormality of the user (patient) can be recognized by the nurse and the doctor. In addition, the notification portion 54 can also be configured to transmit the above-described notification information (warning information) directly to the portable terminal 8 (for a nurse) or the infection management system 7 (for a doctor) via the wireless communication (the wireless communication module 52 and the wireless communication apparatus 5), and can issue the output request for the warning display or the warning sound (alarm or beep sound).

Further, when the body temperature data satisfies a predetermined disease management condition, the notification portion 54 notifies the user and/or the administrator (such as a doctor and a nurse in the embodiment) that the body temperature data does indeed satisfy the predetermined disease management condition. For example, the notification portion 54 is configured to output a warning display or warning sound (alarm or beep sound), for example, when detecting the body temperature at a certain level or more, or a body temperature rise at a certain level or more. Also, in this case, as described above, it is preferable to transmit notification information (warning information) to the electronic medical chart system 6 via the wireless communication (wireless communication module 52 and wireless communication apparatus 5).

Further, the notification portion 54 can be configured to notify that the measurement abnormality is detected when the body temperature data cannot be acquired for a predetermined time or longer. For example, the notification portion 54 outputs an alarm as the measurement abnormality when the body temperature data cannot be acquired for 30 minutes or more. Also, in this case, as described above, it is preferable to transmit notification information (warning information) to the electronic medical chart system 6 via the wireless communication (wireless communication module 52 and wireless communication apparatus 5).

The wireless communication module 52 is configured to transmit the acquired body temperature data and the above-described notification information (warning information) to the external wireless communication apparatus 5 (electronic medical chart system 6) or the like. Moreover, the wireless communication module 52 is configured to receive, from the wireless communication apparatus 5 (electronic medical chart system 6), the personal characteristic information of the user described above, statistical data (average and standard deviation) for setting the normal temperature range, and the like. In an exemplary aspect, the wireless communication module 52 transmits and receives the information described above by using, for example, Bluetooth® or the like.

In the temperature information processing unit 50, the thin battery 53 is accommodated therein. The battery 53 supplies electric power to the MCU 51, the wireless communication module 52, and the like.

Figure 4:
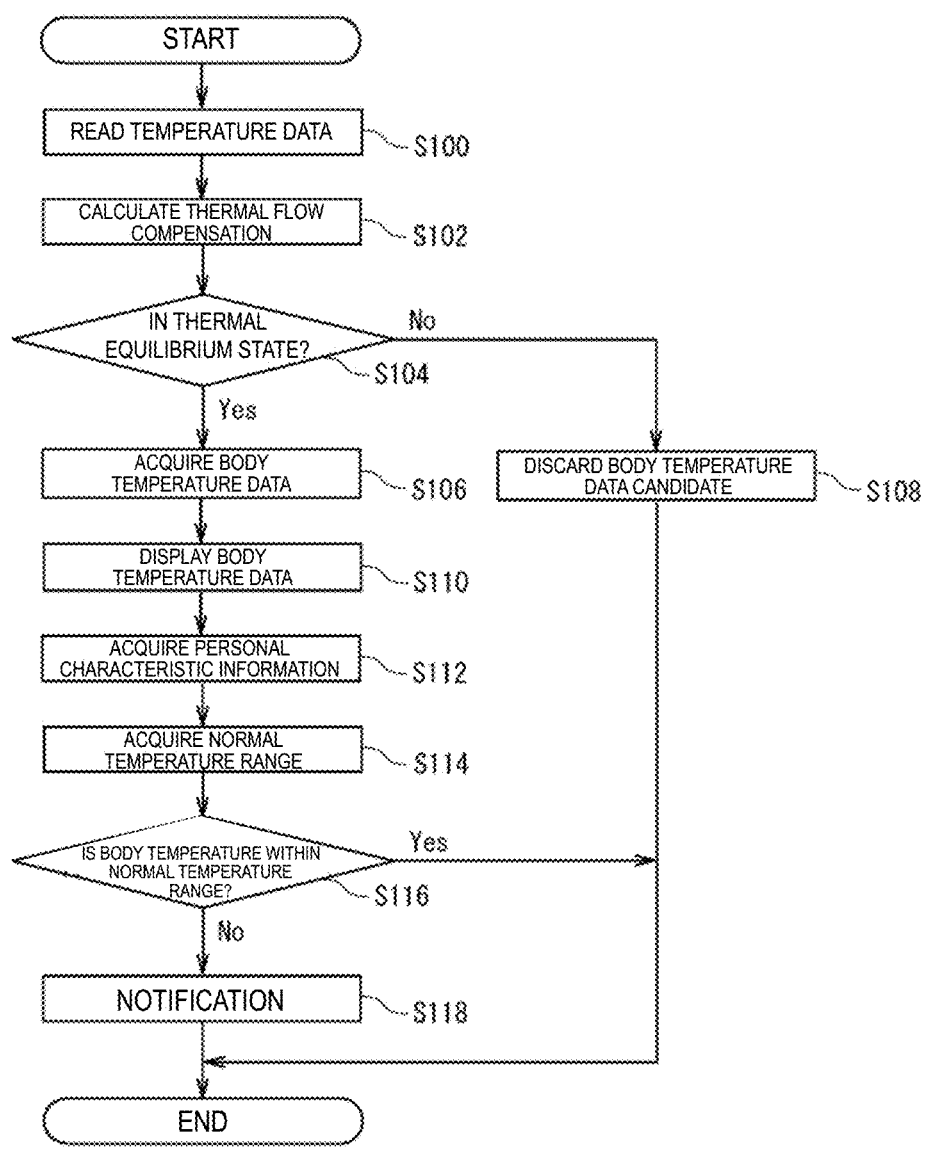
FIG. 4 is a flowchart illustrating a processing procedure of a deep body temperature measurement processing and a body temperature abnormality detection processing by the body temperature measuring device according to the first exemplary embodiment.

Next, an operation of the body temperature measuring device 1 will be described with reference to FIG. 4. FIG. 4 is a flowchart illustrating a processing procedure of deep body temperature measurement processing and body temperature abnormality detection processing by the body temperature measuring device 1. The processing illustrated in FIG. 4 is executed repeatedly at a predetermined timing mainly by the temperature information processing unit 50.

First, in step S100, temperature data detected by each of the temperature sensors 111 to 114 is read.

Next, in step S102, thermal flow compensation calculation is performed on the read temperature data using the above-described thermal flow compensation calculation equations (9) and (10), and a body temperature data candidate is calculated (see, e.g., FIG. 5). Note that since the thermal flow compensation calculation is as described above, detailed description thereof will be omitted here.

Subsequently, in step S104, a determination is made as to whether or not the temperature detection section 11 (temperature sensors 111 to 114) is thermally in an equilibrium state (a state where there is no variation in thermal flow rate) by using the above-described equilibrium state determination equation (1). When it is determined that the thermal equilibrium state is established, the process proceeds to step S106. On the other hand, when it is determined that the thermal equilibrium state is not established, the process proceeds to step S108.

In step S106, the body temperature data candidate calculated in step S102 is acquired as the regular body temperature data, and is output (see FIG. 6). Thereafter, the process proceeds to step S110. In step S108, the body temperature data candidate calculated in step S102 is removed (discarded). Thereafter, the process exits once from this processing.

In step S110, the body temperature data acquired in step S106 is displayed.

Next, in step S112, the personal characteristic information (for example, age, sex, height, weight, etc.) of the user is acquired from the electronic medical record system 6 of the hospital via, for example, wireless communication.

Subsequently, in step S114, a normal temperature range (expected value range of the normal temperature) at each time stored in association with the personal characteristics matching up with the personal characteristics of the user in the category (for example, the same age and sex) is acquired from the normal temperature range (statistical data) stored in advance in association with the personal characteristics.

In step S116, a determination is made as to whether or not the body temperature is within a normal temperature range at the same time. Here, when the body temperature is within the normal temperature range, the process exits once from this processing (for example, without outputting warning display or warning sound). On the other hand, when the body temperature is outside the normal temperature range, the process proceeds to step S118.

In step S118, a notification is provided that the body temperature data is outside the normal temperature range. That is, for example, the warning display or the warning sound indicating that the body temperature data is outside the normal temperature range is output.

As described in detail above, according to the embodiment, the temperature detection section 11 (e.g., four temperature sensors 111 to 114) is determined whether or not to be thermally in the equilibrium state by using the equilibrium state determination equation (1), and body temperature data is acquired based on the temperature data detected when the temperature detection section 11 is determined to be in the thermal equilibrium state. For this reason, for example, even though the temperature detection section 11 is temporarily made into the non-equilibrium state due to such as a sudden change (disturbance) in the ambient temperature with a person entering or exiting a room or the like, it is possible to recognize that the non-equilibrium state is reached (in the non-equilibrium state), thereby removing an inaccurate body temperature data candidate/temperature data (noise). Further, since noise (body temperature data candidate in the non-equilibrium state/temperature data) can be removed as described above, it is not necessary to smooth data by providing a low pass filter or the like having a large time constant, for example. As a result, the influence of disturbance can be appropriately eliminated, and heat generation can be grasped in a shorter time (span).

According to the exemplary embodiment, the personal characteristic information (for example, age, sex, height, weight and the like) of the user is acquired, and based on the acquired personal characteristic information of the user and the normal temperature range (expected value range of the normal temperature) stored in association with the personal characteristics, the normal temperature range (expected value range of the normal temperature) of the user is set. That is, the normal temperature range is individually set from statistical data matching with the personal characteristics of the user. Then, it is determined whether or not the body temperature data is within the set normal temperature range. Therefore, for example, heat generation (body temperature abnormality) or the like which is out of the normal temperature range can be detected early and accurately.

According to the exemplary embodiment, the normal temperature range (the expected value range of the normal temperature) of the user is set at each time in association with the time of the day. For this reason, for example, it is possible to take into account the daily variation in body temperature, and it is possible to detect heat generation deviated away from the normal temperature range more accurately. As a result, a fever of the patient in the hospital can be detected accurately and early, regardless of the day and night, for example.

According to the exemplary embodiment, the body temperature data of the user acquired in the past is learned, and the user's normal temperature range (the expected value range of the normal temperature) is set (or corrected) in consideration of the learned learning value. Therefore, it is possible to further enhance the likelihood of the normal temperature range for each user due to the learning effect.

According to the exemplary embodiment, when the body temperature data falls outside the normal temperature range, the user and/or the administrator (doctor or nurse) is informed that the body temperature data falls outside the normal temperature range. Therefore, when it is detected that the body temperature data falls outside the normal temperature range, the user and/or the administrator can recognize that the body temperature data has fallen outside the normal temperature range (have a fever). As a result, for example, a fever of the patient can be determined accurately and early in the hospital regardless of the day and night, and the countermeasure activity such as treatment can be started early. In particular, when the body temperature of an inpatient or the like is continuously measured and a fever alarm is intended to be issued, it is possible to perform the function continuously for long time only by sticking the sensor to the trunk of the inpatient without requiring special labor such as inserting a thermometer beneath the tongue or armpit of the inpatient.

According to the exemplary embodiment, when the body temperature data satisfies a predetermined disease management condition, the user and/or the administrator (doctor or nurse) is notified that the body temperature data satisfies the predetermined disease management condition. For this reason, for example, such as when the body temperature or the body temperature rise at certain level or more is detected, it is possible to cause the user and/or the administrator to recognize the body temperature or the body temperature rise at a certain level or more.

According to the exemplary embodiment, the measurement abnormality is notified when the body temperature data is not acquired for a predetermined time (for example, 30 minutes) or more (for example, warning display or warning sound (alarm) is output). Therefore, the user (doctor or nurse) or the like can recognize the measurement abnormality early.

Second Exemplary Embodiment

Figure 7:
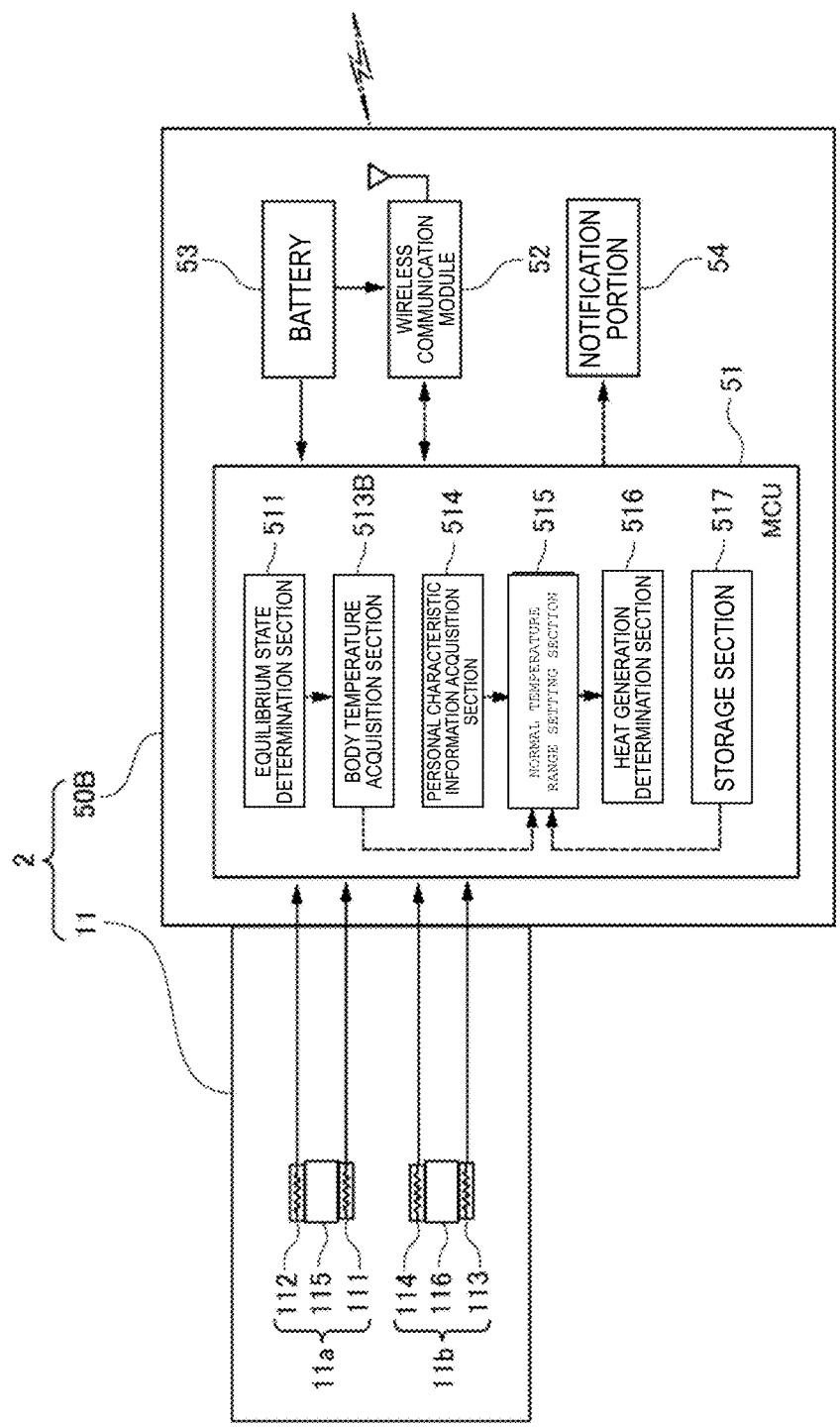
FIG. 7 is a block diagram illustrating a functional configuration of a body temperature measuring device according to a second exemplary embodiment.
Figure 8:
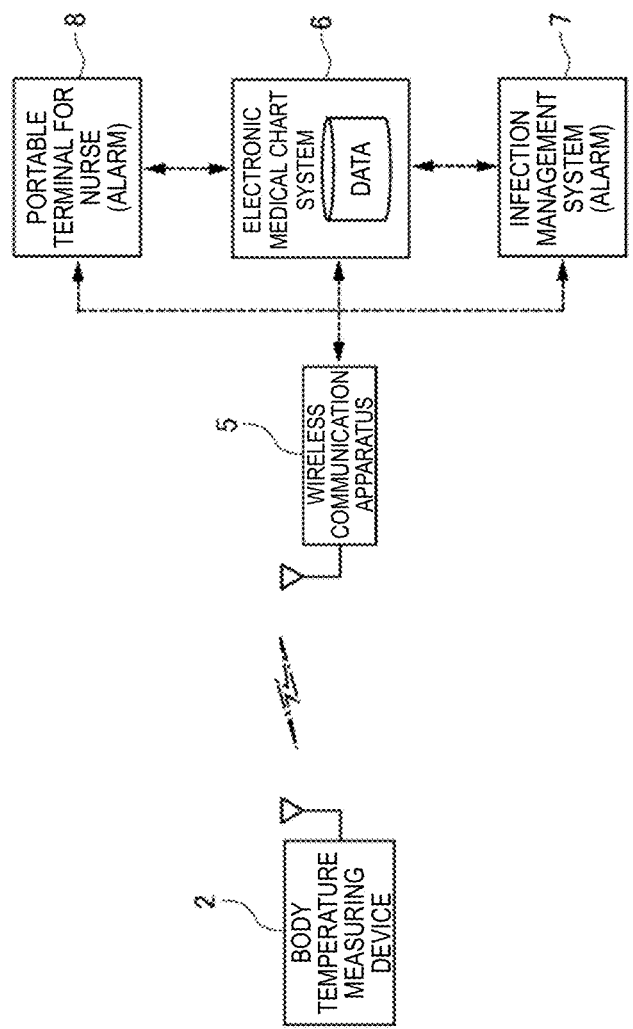
FIG. 8 is a block diagram illustrating an overall configuration of an intra-hospital system to which the body temperature measuring device according to the second exemplary embodiment is applied.

Next, a body temperature measuring device 2 according to a second exemplary embodiment will be described with reference to FIG. 7 together with FIG. 8. Here, a description of the configuration of the same as or similar to that of the above-described first embodiment will be simplified or omitted, and different points will be mainly described. FIG. 7 is a block diagram illustrating a functional configuration of the body temperature measuring device 2. FIG. 8 is a block diagram illustrating an overall configuration of an intra-hospital system to which the body temperature measuring device 2 is applied. It is noted that the same reference signs are given to constituent elements which are the same as or equivalent to those in the first embodiment in FIG. 7 and FIG. 8 and the details will not be repeated herein.

The body temperature measuring device 2 is different from the body temperature measuring device 1 according to the first embodiment described above in that a temperature information processing unit 50B is provided instead of the temperature information processing unit 50. Further, it is different from the body temperature measuring device 1 in that the temperature information processing unit 50B includes a body temperature acquisition section 513B instead of the body temperature acquisition section 513. It is noted that since other configurations are the same as or similar to those of the body temperature measuring device 1 described above, a detailed description thereof will be omitted here.

The body temperature acquisition section 513B is configured to first obtain a body temperature data candidate (or a correction value) acquired based on the detected temperature data, perform statistical processing (for example, k-means clustering or Ward's method) on the body temperature data candidate, and cluster the body temperature data candidate. Since the method of obtaining the body temperature data candidate is the same as that of the first embodiment described above, a detailed description thereof will be omitted here. In the embodiment, the k-means clustering is used for statistical processing, and the body temperature data candidates are clustered (stratified) into three layers.

Figure 10:
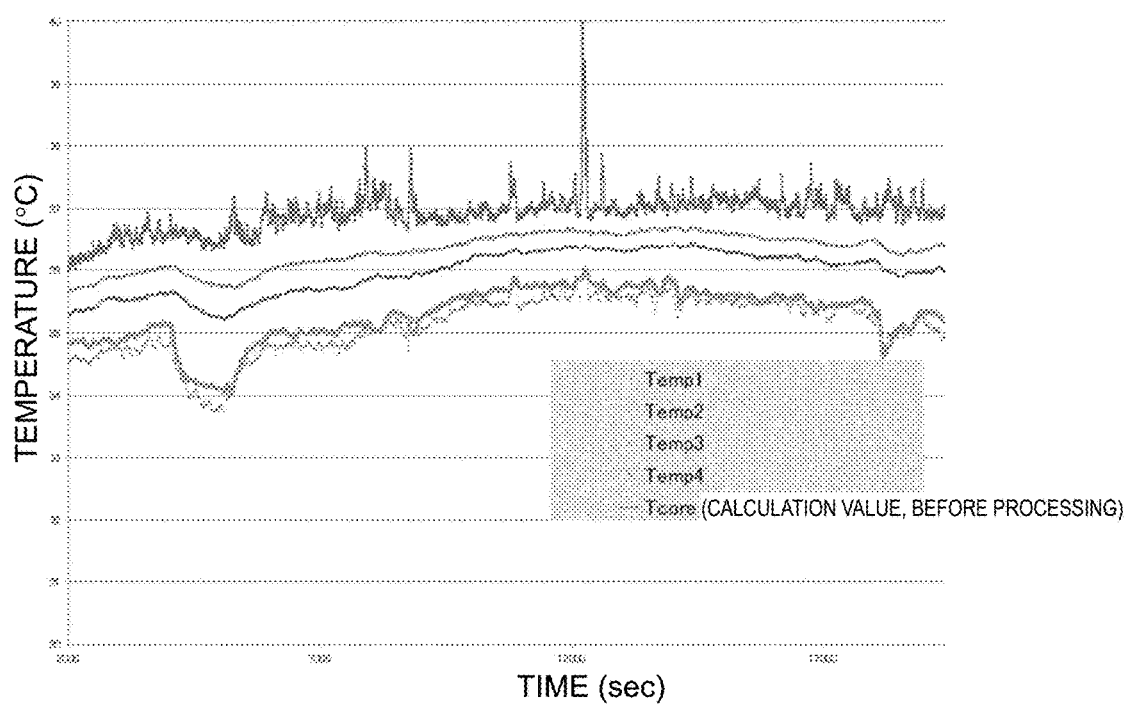
FIG. 10 is a diagram illustrating an example of a body temperature data candidate (thermal flow compensation calculation result) before performing statistical processing (clustering).
Figure 11:
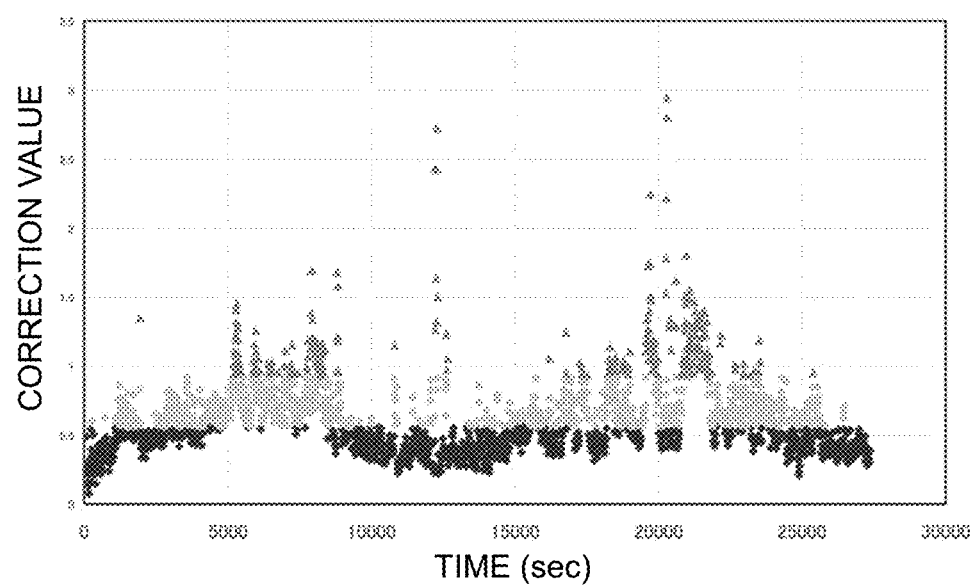
FIG. 11 is a diagram illustrating an example of a body temperature data candidate (stratification determination result of thermal flow compensation calculation) after performing statistical processing (clustering).

Here, FIG. 10 illustrates an example of a body temperature data candidate (thermal flow compensation calculation result) before performing the statistical processing (clustering). Further, FIG. 11 illustrates an example of a body temperature data candidate (stratification determination result of the thermal flow compensation calculation) after performing the statistical processing (clustering). It is noted that in FIG. 10 and FIG. 11, the horizontal axis represents time, and the vertical axis represents temperature or a correction value (° C.).

Next, the body temperature acquisition section 513B acquires body temperature data from a body temperature data candidate belonging to a cluster that does not include a body temperature data candidate obtained from temperature data detected when the temperature detection section 11 is determined to be thermally in a non-equilibrium state (i.e., a cluster composed of only body temperature data candidates obtained from temperature data detected when the temperature detection section 11 is thermally in an equilibrium state). Since a method for determining whether or not the temperature detection section 11 is thermally in the non-equilibrium state is as described above, a detailed description thereof will not be repeated here.

Figure 12:
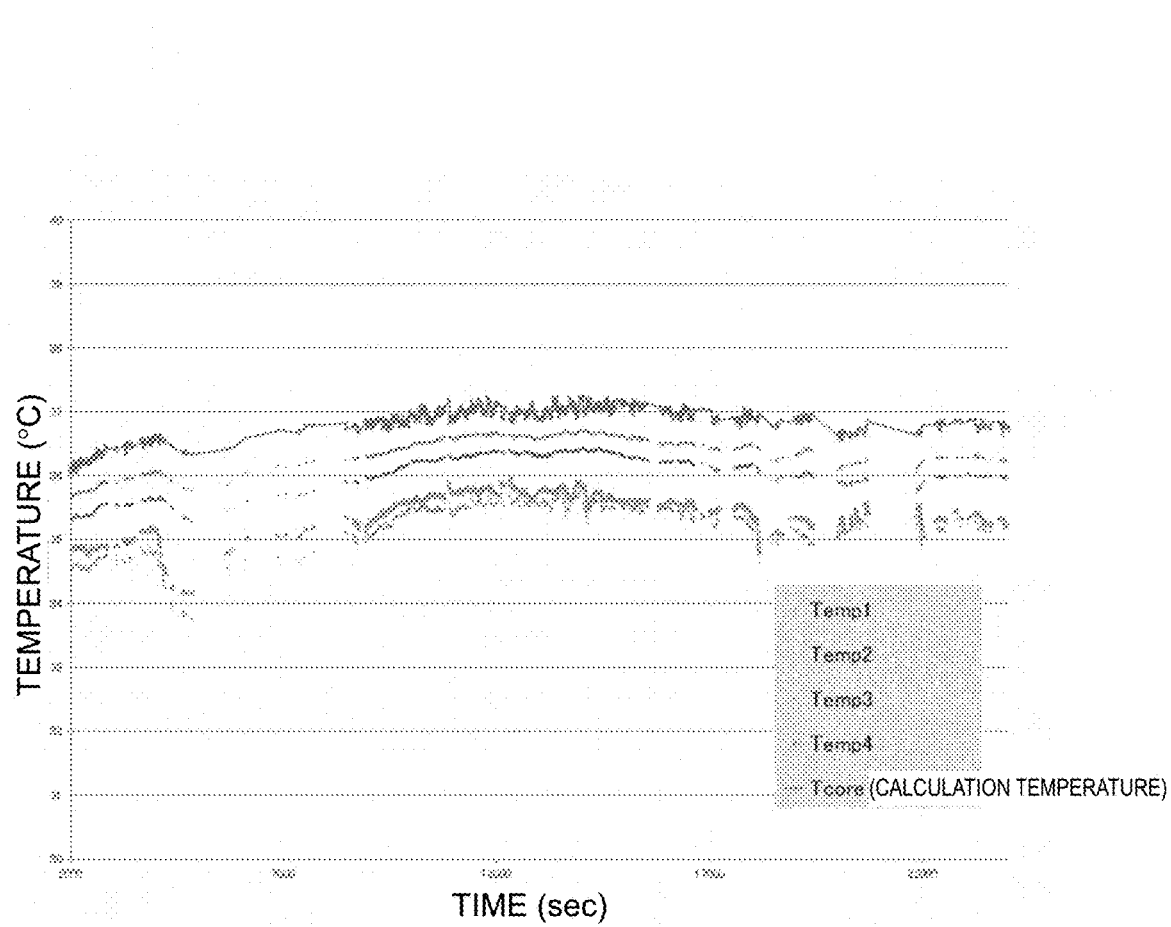
FIG. 12 is a diagram illustrating an example of body temperature data (compensation calculation result and body temperature calculation value) after removal of a cluster to be removed (data) after clustering (stratification determination).

Here, FIG. 12 illustrates an example of body temperature data (compensation calculation result and body temperature calculation value) after removal of the cluster (data) to be removed after clustering (stratification determination). It is noted that in FIG. 12, the horizontal axis represents time, and the vertical axis represents temperature (° C.).

Figure 9:
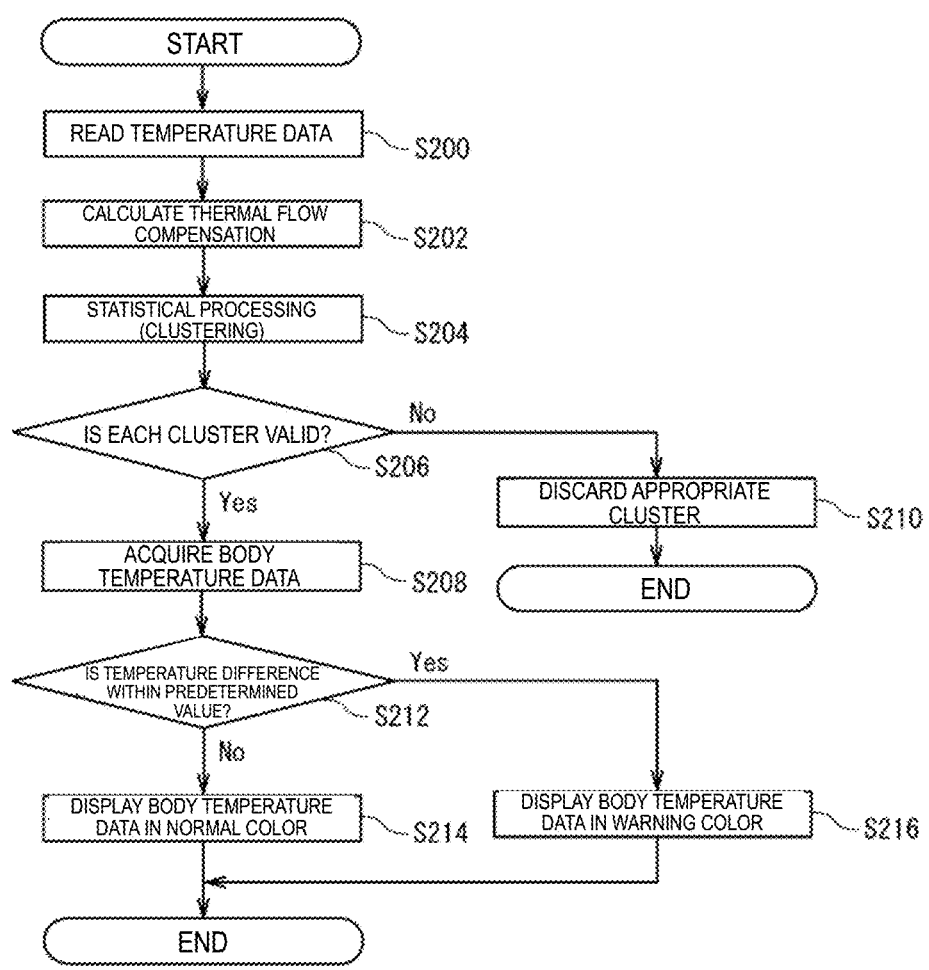
FIG. 9 is a flowchart illustrating a processing procedure of a deep body temperature measurement processing and a body temperature abnormality detection processing by the body temperature measuring device according to the second exemplary embodiment.

Next, an operation of the body temperature measuring device 2 will be described with reference to FIG. 9. FIG. 9 is a flowchart illustrating the processing procedure of the deep body temperature measurement processing and the body temperature abnormality detection processing by the body temperature measuring device 2. The processing illustrated in FIG. 9 is executed repeatedly at a predetermined timing by the temperature information processing unit 50B mainly.

First, in step S200, the temperature data detected by the temperature sensors 111 to 114 are read.

Next, in step S202, the thermal flow compensation calculation is performed on the read temperature data by using the above-described thermal flow compensation calculation equations (9) and (10), and a body temperature data candidate is calculated (see FIG. 10). It is noted that since a method of calculating the body temperature data candidate is as described above, a detailed description thereof will not be repeated.

Subsequently, in step S204, clustering (stratification) is performed using the k-means clustering for the body temperature data candidates that have been continuously measured (acquired) for a certain period of time (see FIG. 11). It is noted that since the details of clustering are as described above, a detailed description thereof will be omitted here.

Subsequently, in step S206, a determination is made as to whether or not each cluster (layer) is a valid cluster by using the above-described equilibrium state determination equation (1). That is, a determination is made as to whether or not is a cluster that does not include a body temperature data candidate acquired from temperature data detected when it is not in a thermal equilibrium state. Here, when it is determined that the cluster is a valid cluster, the process proceeds to step S208. On the other hand, when it is determined that the cluster is not a valid cluster, the process proceeds to step S210.

In step S208, the body temperature data candidate included in the cluster determined to be valid is acquired as the regular body temperature data, and then is output (see FIG. 12). Thereafter, the process proceeds to step S212. On the other hand, in step S210, the cluster (body temperature data candidate included in the cluster) determined to be invalid is removed (discarded). Thereafter, the process exits once from this processing.

In step S212, a determination is made as to whether or not a deviation between the acquired body temperature data and the average of the body temperature data measured at the same time until the previous day is within a predetermined 24-hour variation value. Here, when the deviation is within the variation value, the process proceeds to step S214. When the deviation is outside the variation value, the process proceeds to step S216.

In step S214, the body temperature data is displayed in a normal color (for example, a blue color), and then, the process exits once from this processing. In contrast, in step S216, the body temperature data is displayed in a warning color (for example, a red color), and then, the process exits once from this processing.

According to the embodiment, the body temperature data candidate is obtained based on the detected temperature data, and statistical processing is performed on the body temperature data candidate, whereby the body temperature data candidate is clustered. Then, the body temperature data is acquired from the body temperature data candidates belonging to the cluster that does not include the body temperature data candidate obtained from the temperature data detected when the temperature detection section 11 is determined to be thermally in the non-equilibrium state. For this reason, for example, even though the temperature detection section 11 is temporarily made into the non-equilibrium state due to such as a sudden change (disturbance) in the ambient temperature with a person entering or exiting a room or the like, it is possible to recognize that the non-equilibrium state is reached (in the non-equilibrium state), thereby removing the cluster including the body temperature data candidate obtained from the inaccurate temperature data (noise) detected when it is in the non-equilibrium state. As a result, the influence of disturbance can be eliminated more reliably.

Third Exemplary Embodiment

Figure 13:
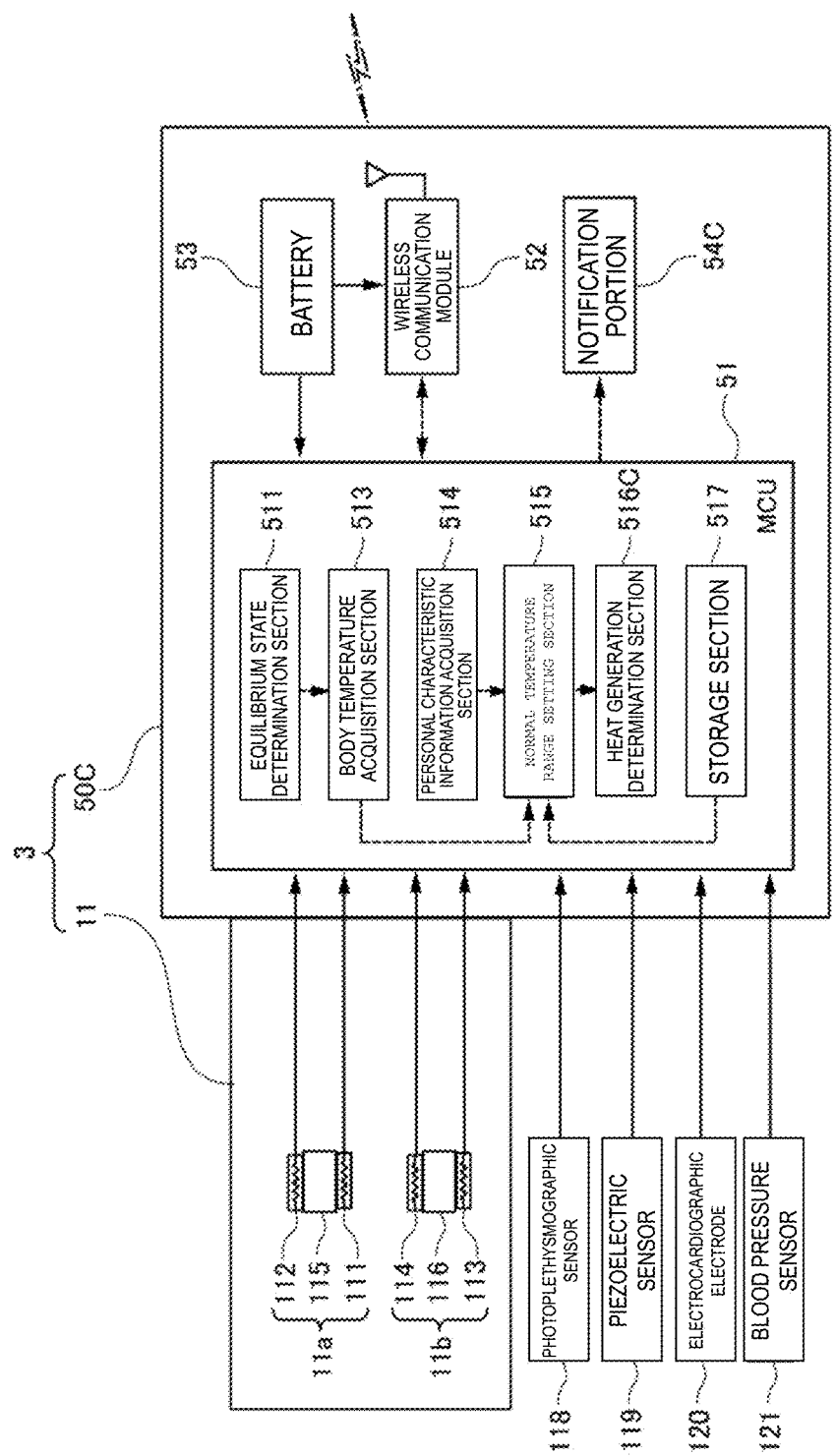
FIG. 13 is a block diagram illustrating a functional configuration of a body temperature measuring device according to a third exemplary embodiment.

Next, with reference to FIG. 13 together with FIG. 14, a description will be given of a body temperature measuring device 3 according to a third embodiment. Here, a description of the configuration of the same as or similar to that of the above-described first embodiment will be simplified or omitted, and different points will be mainly described. FIG. 13 is a block diagram illustrating a functional configuration of the body temperature measuring device 3. FIG. 14 is a block diagram illustrating an overall configuration of an intra-hospital system to which the body temperature measuring device 3 is applied. It is noted that the same reference signs are given to constituent elements which are the same as or equivalent to those in the first embodiment in FIG. 13 and FIG. 14.

The body temperature measuring device 3 is different from the body temperature measuring device 1 according to the above-described first embodiment in that a photoplethysmographic sensor 118 for detecting a photoplethysmographic signal (e.g., a pulse rate), a piezoelectric sensor 119 for detecting respiration rate, an electrocardiographic electrode 120 for detecting an electrocardiographic signal (heart rate), and a blood pressure sensor 121 for detecting blood pressure are provided in addition to the four temperature sensors 111 to 114. It is noted that the photoplethysmographic sensor 118, the piezoelectric sensor 119, the electrocardiographic electrode 120, and the blood pressure sensor 121 can generally provide a biological information measuring unit according to an exemplary aspect.

The body temperature measuring device 3 is different from the body temperature measuring device 1 according to the above-described first embodiment in that a temperature information processing unit 50C is provided instead of the temperature information processing unit 50. Moreover, it is different from the body temperature measuring device 1 described above in that the temperature information processing unit 50C includes a heat generation determination section 516C instead of the heat generation determination section 516, and includes a notification portion 54C instead of the notification portion 54. Since other configurations are the same as or similar to those of the body temperature measuring device 1 described above, a detailed description thereof will be omitted here.

In addition to the determination of the heat generation (e.g., whether or not the body temperature is within the normal temperature range), the heat generation determination section 516C determines whether or not the body temperature data and biological information (for example, heart rate, respiration rate, etc.) satisfy a predetermined disease management condition. When it is determined that the body temperature data and the biological information satisfy the predetermined disease management condition, the notification portion 54C notifies a user and/or an administrator (doctor or nurse) that the body temperature data and the biological information satisfy the predetermined disease management condition. Specific examples are listed below.

An example of a Suspicion of Sepsis (Systemic Inflammatory Response Syndrome)

When any two or more items of the following conditions (1), (2), and (3) are satisfied, warning display or warning sound (alarm) is output from the notification portion 54C as a suspicion of sepsis (systemic inflammatory response syndrome).

body temperature>38° C. or body temperature<36° C.
heart rate>90 times/min
respiration rate>20 times/min 2. An example of a Suspicion of Surgical Site (Deep Incision) Wound Infection When the patient within 30 days after the surgery falls under the item of "body temperature>38° C.", warning display or warning sound (alarm) is output from the notification portion 54C as a suspicion of a surgical site (deep incision) wound infection.

3. An example of a Suspicion of Catheter Blood Stream Infection

When the item of "body temperature>39° C." or "systolic blood pressure (maximum value)<100 mmHg" is satisfied, warning display or warning sound (alarm) is output from the notification portion 54C as a suspicion of a catheter blood stream infection.

4. An example of a Suspicion of Relative Bradycardia (Bacterial Infection/Drug Fever/Tumor Fever)

When the following conditions (1) and (2) are satisfied, warning display or warning sound (alarm) is output from the notification portion 54C as a suspicion of a relative bradycardia (bacterial infection/drug fever/tumor fever).

heart rate<110 times/min at body temperature>39° C.
heart rate<120 times/min at body temperature>40° C.

5. An example of a Suspicion of Clostridium (CD) Enteritis

When the patient aged 65 or more years falls under the item of "body temperature>38.3° C.", warning display or warning sound (alarm) is output from the notification portion 54C as a suspicion of a Clostridium (CD) enteritis.

6. An example of a Suspicion of Fastigium of Acute Pneumonia, Japanese Encephalitis, Children's Dysentery, Typhoid When under the conditions of "body temperature>39° C." and "variation in the day is within one degree", warning display or warning sound (alarm) is output from the notification portion 54C as a suspicion of the fastigium of acute pneumonia, Japanese encephalitis, children's dysentery, and typhoid.

7. An example of a Suspicion of Continuous Fever

When under the conditions of high temperature of "body temperature≥39 degrees or more" and "variation in the day is within one degree (little variation)", warning display or warning sound (alarm) is output from the notification portion 54C as a suspicion of continuous fever.

8. An example of a Suspicion of Sepsis, Pyelonephritis, Cystitis, Tuberculosis, Influenza, Lung Abscesses, or Salpingitis When the state of "body temperature>37.2° C." lasts for equal to or more than one day, and conditions of "maximum body temperature>39° C." and "intra-day variation is one degree or more" are satisfied, warning display or warning sound (alarm) is output from the notification portion 54C as a suspicion of sepsis, pyelonephritis, cystitis, tuberculosis, influenza, lung abscesses, or salpingitis.

9. An example of a Suspicion of Remittent Fever

When under the conditions of "maximum body temperature in one day is 39 degrees or more" and "variation in one day is one degree or more" (when the temperature varies greatly but does not fall down to the normal temperature), warning display or warning sound (alarm) is output from the notification portion 54C as a suspicion of remittent fever.

10. An example of a Suspicion of Malaria, Sepsis, or Pyelonephritis

When the conditions of "body temperature>39° C." and "body temperature<37.2° C." (both) are satisfied in one day, warning display or warning sound (alarm) is output from the notification portion 54C as a suspicion of malaria, sepsis, or pyelonephritis.

11. An example of a Suspicion of Intermittent Fever

When the conditions of "body temperature>39° C." and "body temperature<normal temperature" (both) are satisfied in one day, warning display or warning sound (alarm) is output from the notification portion 54C as a suspicion of an intermittent fever.

12. An example of a Fever of Unknown Origin

When the above-described other conditions are not satisfied at the state of "body temperature>38.3° C.", warning display or warning sound (alarm) is output from the notification portion 54C as a fever of unknown origin.

According to the exemplary embodiments, in addition to the body temperature data, other biological information (for example, heart rate, pulse rate, respiration rate, blood pressure, etc.) is simultaneously measured, and when the body temperature data and the biological information satisfy predetermined disease management conditions, the user and/or the administrator (such as a doctor, a nurse, or the like) is notified that the body temperature data and the biological information satisfy the predetermined disease management conditions. For this reason, for example, a combination of body temperature (heat generation) and other biological information (for example, heart rate, pulse rate, respiration rate, blood pressure, etc.) can be used to detect and notify the presence of the above-described specific disease risk.

While the exemplary embodiments of the present invention have been described above, it is noted that the present invention is not intended to be limited to the embodiments described above, and various modifications may be made. For example, although the embodiment has been described with reference to the case where the present invention is applied to the intra-hospital system, the present invention may be used alone, or may be applied to, for example, a system in an elderly facility instead of the intra-hospital system.

Further, a configuration may be adopted in which a part of the function of the body temperature measuring device 1 (2, 3) described above is provided on the intra-hospital system side (the electronic medical chart system 6 or the infection management system 7 side).

In the above embodiment, although the body temperature data candidate is calculated from the temperature data, and then the body temperature data candidate calculated from the temperature data detected when the temperature detection section 11 is in the non-equilibrium state is removed so that the regular body temperature data is acquired, instead of such a configuration, for example, a configuration may be adopted in which the body temperature data is acquired using the temperature data obtained after removal of the temperature data (noise) detected when the temperature detection section 11 is in the non-equilibrium state.

Further, in the above-described embodiment, although the temperature detection section 11 includes two sets of sensing portions 11a and 11b, when the thermal resistance RB of the human body can be acquired, the temperature detection section 11 may have a set of sensing portion.

REFERENCE SIGNS LIST 1, 2, 3 BODY TEMPERATURE MEASURING DEVICE
11 TEMPERATURE DETECTION SECTION
110 FLEXIBLE SUBSTRATE
111 FIRST TEMPERATURE SENSOR
112 SECOND TEMPERATURE SENSOR
113 THIRD TEMPERATURE SENSOR
114 FOURTH TEMPERATURE SENSOR
115, 116 THERMAL RESISTOR
117 HEAT-INSULATING MEMBER
118 PHOTOPLETHYSMOGRAPHIC SENSOR
119 PIEZOELECTRIC SENSOR
120 ELECTROCARDIOGRAPHIC ELECTRODE
121 BLOOD PRESSURE SENSOR
50, 50B, 50C TEMPERATURE INFORMATION PROCESSING UNIT
51 MCU
511 EQUILIBRIUM STATE DETERMINATION SECTION
513, 513B BODY TEMPERATURE ACQUISITION SECTION
514 PERSONAL CHARACTERISTIC INFORMATION ACQUISITION SECTION
515 NORMAL TEMPERATURE RANGE SETTING SECTION
516, 516C HEAT GENERATION DETERMINATION SECTION
517 STORAGE SECTION (MEMORY)
52 WIRELESS COMMUNICATION MODULE
53 BATTERY
54, 54C NOTIFICATION PORTION

The invention claimed is:

1. A body temperature measuring device comprising:
a temperature detector configured to detect temperature data and that includes a thermal resistor and a plurality of temperature sensors that sandwich the thermal resistor or are embedded in the thermal resistor;

an equilibrium state determination unit configured to determine whether the temperature detector is in a thermal equilibrium state based on the temperature data detected by the plurality of temperature sensors; and a body temperature acquisition unit configured to acquire body temperature data based on the detected temperature data when the temperature detector is determined to be in the thermal equilibrium state, and based on a physical property value of the thermal resistor, wherein the body temperature acquisition unit is configured to obtain a body temperature data candidate based on the detected temperature data, cluster the body temperature data candidate, and acquire the body temperature data from a respective body temperature data candidate belonging to a cluster that does not include a respective body temperature data candidate obtained from the detected temperature data when the temperature detector is determined to not be in the thermal equilibrium state.

2. The body temperature measuring device according to claim 1, wherein the plurality of temperature sensors comprises a first temperature sensor configured to detect temperature data T11, a second temperature sensor configured to detect temperature data T2, a third temperature sensor configured to detect temperature data T3, and a fourth temperature sensor configured to detect temperature data T4.

3. The body temperature measuring device according to claim 2, wherein the equilibrium state determination unit is configured to determine the temperature detector is in the thermal equilibrium state when $T3-T4>T1-T2$, with $T3>T1$.

4. The body temperature measuring device according to claim 3, wherein the equilibrium state determination unit is configured to determine the temperature detector is in the thermal equilibrium state when:

$$dTa>dT4,$$

$$K(T1-T2)-(T3-T4)>0 \text{ (when } Ta>Tb\text{), and}$$

$$K(T1-T2)-(T3-T4)\leq 0 \text{ (when } Ta\leq Tb\text{),}$$

wherein K is a constant of a ratio of thermal resistance in two thermal flows, and wherein Ta is an ambient temperature and Tb is a temperature data candidate for the body temperature data.

5. The body temperature measuring device according to claim 2, wherein the equilibrium state determination unit is configured to determine the temperature detector is in the thermal equilibrium state when:

$$\Delta T3<a,$$

$$\Delta T1<a,$$

$$\Delta T3<\Delta T4, \text{ and}$$

$$\Delta T1<\Delta T2,$$

wherein a is a predetermined value of temperature over time.

6. The body temperature measuring device according to claim 5, wherein a is 0.2° C./minute.

7. The body temperature measuring device according to claim 1, further comprising:

an acquisition unit configured to acquire personal characteristic information of a user;

a storage unit configured to store personal characteristics associated with a normal temperature range;

a setting unit configured to set a normal temperature range of the user based on the acquired personal characteristic information and a respective normal temperature range associated with the personal characteristics; and a determination unit configured to determine whether the acquired body temperature data is within the normal temperature range set by the setting unit.

8. The body temperature measuring device according to claim 7, wherein the setting unit is further configured to set the normal temperature range of the user based on a time of a day.

9. The body temperature measuring device according to claim 7, wherein the setting unit is further configured to learn the acquired body temperature data of the user, and to set the normal temperature range of the user based on a learning value.

10. The body temperature measuring device according to claim 7, further comprising a notification unit configured to notify the user that the acquired body temperature data is outside the set normal temperature range.

11. The body temperature measuring device according to claim 10, wherein the notification unit is configured to notify that a measurement abnormality is detected when the acquired body temperature data is not acquired for at least a predetermined time.

12. The body temperature measuring device according to claim 10, further comprising:

a biological information measuring unit configured to measures additional biological information separate from the acquired body temperature data, wherein the notification unit is configured to notify the user that the acquired body temperature data and the measured additional biological information satisfy a predetermined disease management condition.

13. The body temperature measuring device according to claim 7, further comprising a notification unit configured to notify the user that the acquired body temperature data satisfies a predetermined disease management condition.

14. The body temperature measuring device according to claim 13, wherein the notification unit is configured to notify that a measurement abnormality is detected when the acquired body temperature data is not acquired for at least a predetermined time.

15. The system of claim 1, wherein the equilibrium state determination unit includes a processor configured to execute instructions stored in memory to determine whether the temperature detector is in the thermal equilibrium state, and the body temperature acquisition unit includes a processor configured to execute instructions stored in memory to acquire the body temperature data based on the detected temperature data and the physical property value of the thermal resistor.

16. A method for measuring body temperature, the method comprising:

detecting temperature data by a temperature detector that includes a thermal resistor and a plurality of temperature sensors that sandwich the thermal resistor or are embedded in the thermal resistor;

determining whether the temperature detector is in a thermal equilibrium state based on the temperature data detected by the plurality of temperature sensors; and acquiring body temperature data based on the detected temperature data when the temperature detector is determined to be in a thermal equilibrium state, and based on a physical property value of the thermal resistor, wherein the acquiring of the body temperature data comprises obtaining a body temperature data candidate based on the detected temperature data, clustering the body temperature data candidate, and acquiring the body temperature data from a respective body temperature data candidate belonging to a cluster that does not include a respective body temperature data candidate obtained from the detected temperature data when the temperature detector is determined to not be in the thermal equilibrium state.

17. The method according to claim 16, wherein the plurality of temperature sensors include a first temperature sensor that detects temperature data T1, a second temperature sensor that detects temperature data T2, a third temperature sensor that detects temperature data T3, and a fourth temperature sensor that detects temperature data T4, and wherein the method further comprises determining the temperature detector is in the thermal equilibrium state when T3−T4>T1−T2, with T3>T1.

18. The method according to claim 17, further comprising determining the temperature detector is in the thermal equilibrium state when:

$dTa > dT4$, $K(T1-T2)-(T3-T4) > 0$ (when $Ta > Tb$), and $K(T1-T2)-(T3-T4) \leq 0$ (when $Ta\ Tb$), wherein K is a constant of a ratio of thermal resistance in two thermal flows, and wherein Ta is an ambient temperature and Tb is a temperature data candidate for the body temperature data.

19. The method according to claim 16, wherein the plurality of temperature sensors include a first temperature sensor that detects temperature data T1, a second temperature sensor that detects temperature data T2, a third temperature sensor that detects temperature data T3, and a fourth temperature sensor that detects temperature data T4, and wherein the method further comprises determining the temperature detector is in the thermal equilibrium state when:

$\Delta T3 < a$, $\Delta T1 < a$, $\Delta T3 < \Delta T4$, and $\Delta T1 < \Delta T2$, wherein a is a predetermined value of temperature over time.

\* \* \* \* \*